(12) United States Patent
Heiberger

(10) Patent No.: US 7,686,450 B2
(45) Date of Patent: Mar. 30, 2010

(54) DEVICE FOR MEASURING AND SURGICAL CORRECTION IMAGING ERRORS IN THE HUMAN EYE

(76) Inventor: Kurt Heiberger, Burkhardtstrasse 9, Nuremberg, 90455 (DE)

( * ) Notice: Subject to any disclaimer, the term of this patent is extended or adjusted under 35 U.S.C. 154(b) by 231 days.

(21) Appl. No.: 11/814,915

(22) PCT Filed: Feb. 1, 2006

(86) PCT No.: PCT/DE2006/000192

§ 371 (c)(1),
(2), (4) Date: Jul. 26, 2007

(87) PCT Pub. No.: WO2006/081814

PCT Pub. Date: Aug. 10, 2006

(65) Prior Publication Data

US 2008/0165320 A1    Jul. 10, 2008

(30) Foreign Application Priority Data

Feb. 1, 2005   (DE) .................. 10 2005 005 564

(51) Int. Cl.
  *A61B 3/14* (2006.01)
  *A61B 3/10* (2006.01)
(52) U.S. Cl. ............................. 351/206; 351/205
(58) Field of Classification Search .......... 351/206–208
   See application file for complete search history.

(56) References Cited

U.S. PATENT DOCUMENTS

| | | | | |
|---|---|---|---|---|
| 5,997,141 A | * | 12/1999 | Heacock | 351/221 |
| 6,997,555 B2 | * | 2/2006 | Dick et al. | 351/211 |
| 2003/0179344 A1 | | 9/2003 | Van de Velde | |
| 2005/0237486 A1 | * | 10/2005 | Su et al. | 351/206 |
| 2008/0291397 A1 | * | 11/2008 | Tesar | 351/221 |

FOREIGN PATENT DOCUMENTS

| | | |
|---|---|---|
| DE | 102 07 535 | 9/2003 |
| EP | 1 231 496 A | 8/2002 |

* cited by examiner

*Primary Examiner*—Jordan M. Schwartz
(74) *Attorney, Agent, or Firm*—Lucas & Mercanti, LLP

(57) ABSTRACT

The invention relates to a device for measuring imaging errors in the human eye, wherein substantial scanning of the lens of the eye with a light beam or laser diode determines the measuring accuracy of local refractive power. Measuring accuracy of locally dependent refractive power is achieved by a two-dimensionally refractable tilting mirror which is embodied in the form of a microscanner mirror with the aid of a piezomotor for positioning and by electrically controllable liquid lenses. As a result, it is possible to manufacture the measuring device as small as possible, enabling it to be integrated in to a processing laser in order to monitor the result of treatment with a laser during individual adaptation of contact lenses, intraocular lenses or surgical correction of the retina in situ and to calculate data of a required correction.

20 Claims, 1 Drawing Sheet

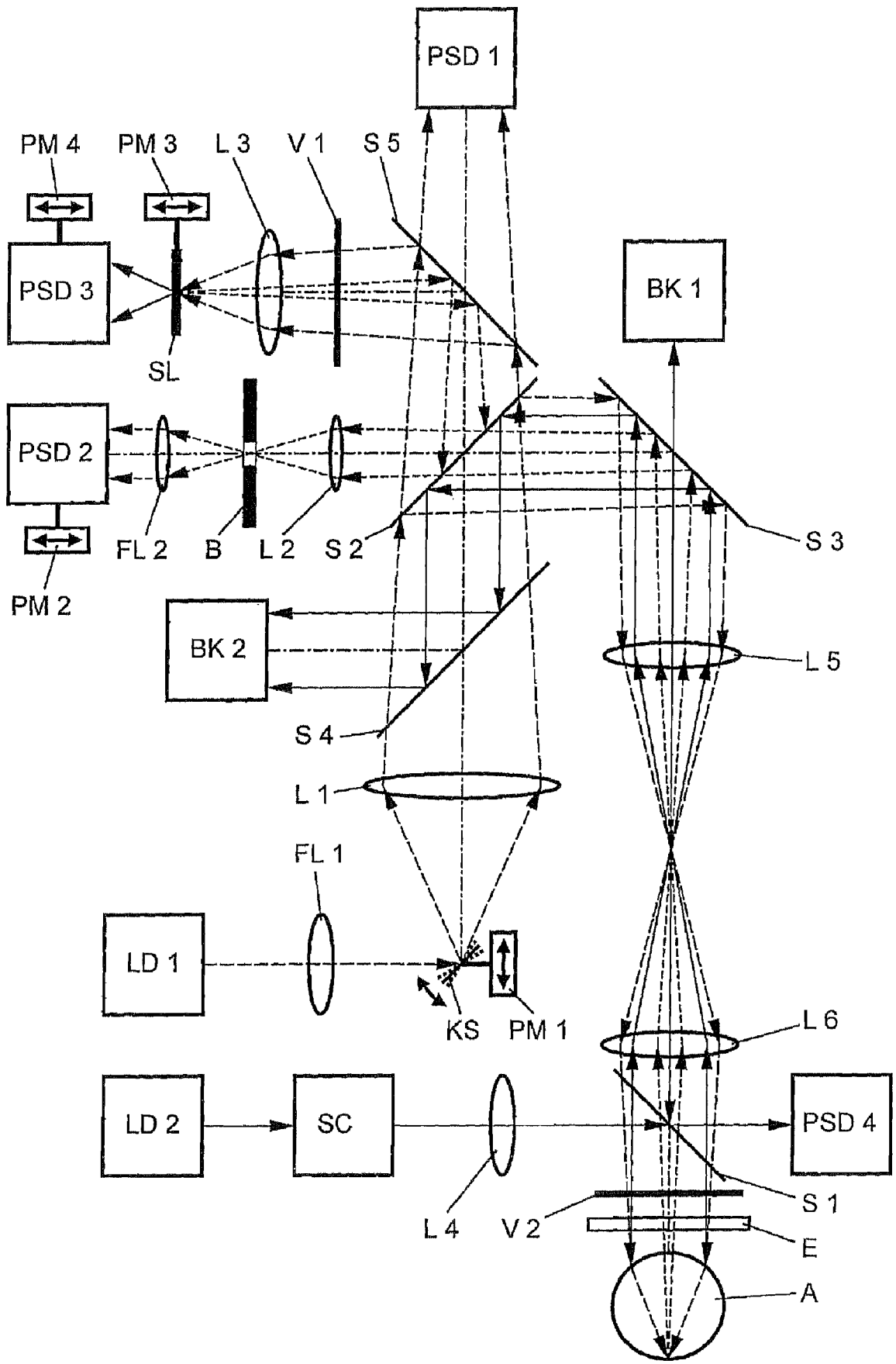

DEVICE FOR MEASURING AND SURGICAL CORRECTION IMAGING ERRORS IN THE HUMAN EYE

BACKGROUND OF THE INVENTION

The invention relates to a device for measuring imaging errors in the human eye, in the case of which the optical system of the eye is scanned with a light beam of a laser diode in an area-wide fashion, and the reflected light beams are measured and evaluated.

US 2005/0007551 A1 discloses such a device and a method having the following method steps: measuring the imaging errors of the entire optical system of the eye and of the shape (radius of curvature) of the cornea and thus its refractive power, and calculating the imaging errors of the cornea from its refractive power, calculating the difference between the values of the imaging errors of the entire optical system of the eye, on the one hand, and of the cornea, on the other hand, storing the calculated values of the imaging errors, and converting these values into a three-dimensionally continuous display.

Because of this three-dimensional distribution of the measured and calculated values of the optical system of the eye, it is possible to check the result of an individual adaptation of contact lenses, of intraocular lenses or a surgical correction of the cornea.

In this known method, which operates with a Hartmann-Shack sensor, the defective vision of the eye is measured with a single laser beam. The number of the image points to be evaluated on the wave front reflected and/or scattered by the retina is limited by the microlens array used. The evaluation of the measurement results lasts approximately 1 s. This method provides only a mean value of the defective vision, for example, existing instances of local defective vision cannot be determined individually, and therefore also cannot be corrected. Consequently, this known method is not suitable for fast conversion of the measurement results in order to use them directly for a simultaneous surgical correction of the optics of the eye.

SUMMARY OF THE INVENTION

It is the object of the invention to provide a method and a device of the type mentioned at the beginning that permit, during the treatment of the eye with a laser system, the screening of the result of the treatment in situ and, simultaneously, to deliver the data for an immediate correction of this result that may be necessary.

This object is achieved by a device having the features of claims 1. Further advantageous refinements of the invention are specified in the dependent claims.

The advantages attained with the invention consist, in particular, in that owing to the integration of the treatment laser into the device for measuring imaging errors, it is possible during surgical treatment of the eye with the treatment laser to read off the result of each individual correction step immediately and, if necessary, to improve it simultaneously. Furthermore, the mechanical and optical outlay is less than in the case of the known measuring device described at the beginning and the spatial resolution is higher, since the measurement object is scanned in an area-wide fashion.

BRIEF DESCRIPTION OF THE DRAWINGS

An exemplary embodiment of the invention is illustrated in the drawing and will be explained in more detail below. The FIGURE shows the measuring, imaging and treatment beam paths of a device according to the invention.

DETAILED DESCRIPTION OF THE PREFERRED EMBODIMENTS

In order to measure imaging errors, including those of higher order, in the human eye A, the optical system of the latter is scanned with a measuring beam of a laser diode LD 1 in an area-wide fashion. The reflected imaging beams are measured and evaluated in order to undertake a surgical intervention on the eye A of the basis of the result. To this end, into the measuring and/or imaging beam path between the laser diode LD 1 and the eye A a beam splitter S 1 is inserted, via which beam splitter S 1 a treatment beam of a treatment laser LD 2 can be coupled in for a surgical correction of the cornea and/or the lens and/or the retina of the eye A.

For the purpose of scanning the eye A a miniature tilting mirror KS is inserted between the laser diode LD 1 and the beam splitter S 1 in the form of a 2D microscanner mirror with the aid of which the measuring beam can be deflected in two dimensions for the purpose of area-wide scanning of the eye A with frequencies of 150 Hz to 32 kHz.

In order to ensure a uniformly high measuring accuracy over the entire measuring range, the divergence of the light beam supplied by the laser diode LD 1 is set with the aid of an electrically controllable liquid lens FL 1 as a function of the defective vision of the eye to be measured, the result being an ensured uniform beam diameter of less than 200 μm.

Inserted into the measuring beam path between the tilting mirror KS and the first beam splitter S 1 is a lens L 1 whose distance from the tilting mirror KS is variable for the precompensation and for the adaptation of the measuring beam to the mean refractive power of the eye A by a piezomotor PM 1. Depending on the measured refractive power, the tilting mirror KS will stand either at the focal point, upstream of the focal point or downstream of the focal point of the lens L 1. The axial displacement by the piezomotor PM 1 positions the tilting mirror in the nm range such that the precompensation of the measuring beam takes place in the region of less than 0.1 dpt.

Furthermore, inserted into the measuring and/or imaging beam path between the lens L 1 and the beam splitter S 1 is a further beam splitter S 2 that decouples a portion of the measuring beam and feeds it to a position detector PSD 1, which can be replaced by a fast, sensitive camera and is at the same distance from the beam splitter S 2 as the eye (A) (not illustrated in the drawing in a fashion true to scale) and detects the position of the measuring beam striking the cornea of the eye A. At the same time, the position detector PSD 1 monitors the laser power and the laser energy of the measuring beam. The measuring beam path is illustrated in the drawing with large dashes.

The imaging beam path, which is illustrated in the drawing with small dashes, is described below. Inserted into the measuring and/or imaging beam path between the beam splitters S 1 and S 2 is a further beam splitter S 3, which splits the beam path of the imaging beams scattered by the retina of the eye A. In order to measure the refractive power of the optical system of the eye A, the first portion of the imaging beams passes via a further lens L 2 and an aperture B, delimiting the solid angle of the imaging beam path, and via a electrically controllable liquid lens FL 2 to a further position detector PSD 2 or to a fast camera with or without image intensifier. The aperture B transmits only the light that leaves the eye A along the optical axis (visual axis). The local refractive power of the eye A on the optical axis is defined as a reference point. The actual position of the received measuring beam is compared with the desired position. The deviation from the desired position is a measure of the local refractive power of eye A to be measured. The imaging beam can be adapted to the position detector PSD 2 or to the camera via an appropriate control of the liquid lens FL 2.

The second portion of the imaging beams passes to an observation camera BK 1 that is equipped with a unit for recording eye movements and/or viewing movements of a test subject (eye tracking), or can optionally be replaced by other optical units such as, for example, by a microscope or a layer thickness measurement unit.

In order to ensure a uniformly high measuring accuracy over the entire measuring range, a piezomotor PM 2 is used to set the position detector PSD 2 as measurement receiver to that position which, depending on the mean refractive power to be measured, ensures a constant image size and thus a uniform resolution. The piezomotor PM 2 can be dispensed with when the controllable liquid lens FL 2 is used. The liquid lens FL 2 ensures a constant image size and thus a uniform measuring accuracy over the entire measuring range. The dynamics of the measuring unit can be enhanced by combining the piezomotor PM 2 with the liquid lens FL 2.

Inserted into the measuring beam path between the lens L 1 and the beam splitter S 2 is a further beam splitter S 4, which deflects the measuring beams reflected at the surface of the cornea of the eye A after further reflections at the beam splitters S 3 and S 2 to an observation camera BK 2 with telecentric lens, as a result of which the distance between the viewing opening E of the measuring unit and the eye A is measured and the radius of curvature of the cornea of the eye A is screened.

Before the refractive power of the eye A is measured, it must be fixed, that is to say it is measured in an unstressed state. In order for the eye A not to accommodate, the tilting mirror KS is used to insert a flashing point or ring as optotype to which the eye A adapts. The point diameter and/or the ring size can be set with the liquid lens FL 1 and the tilting mirror KS. In order for the eye A to respond equally to the brightness and size of the optotype over the entire measuring range, the light power of the laser is adapted, and the image size is controlled via the liquid lens FL 1 and the tilting mirror KS.

Specific patterns can be projected on to the eye A with the aid of temporally tuned laser passes. The pattern can be distorted such that a symmetrical dot pattern is measured with the position detector PSD 2 by taking into account the previously measured local refractive power of the eye A. The distortion of the dot pattern (coma, astigmatism, etc.) is calculated in advance. This can be used as test measurement.

If a technical measurement object is being measured, the eye A is replaced by an "artificial eye" that consists of a lens L 3, a diffuser plate SL and a position detector PSD 3 or a further camera. The measuring and/or imaging beam path for the artificial eye, which can be interrupted by a shutter V 1, is coupled in or out via a beam splitter S 5 that is inserted into the measuring beam path between the beam splitter S 2 and the position detector PSD 1. The diffuser plate SL is brought into a defined distance from the measurement object with a piezomotor PM 3. The position detector PSD 3 can be axially displaced by a piezomotor PM 4. The light scattered by the diffuser plate SL is captured by the position detector PSD 2 via the imaging beam path, and evaluated. The position of the measuring beam scattered by the diffuser plate SL is measured at a small solid angle via the lens L 2 and the aperture B, which transmits only the light that leaves through the middle of the lens L 3. The local refractive power of the lens L 3 in the optical axis is defined as reference point. The actual position of the received laser beam is compared with the desired position. The deviation from a desired position is a measure of the local refractive power of the artificial eye to be measured.

All beam paths are checked by self calibration before each measurement. A shutter V 2, arranged at the viewing opening E for the eye A to be measured, is closed so that no light can shine into the measuring unit from the outside. The shutter V 1 arranged upstream of the artificial eye is opened, and the artificial eye is measured. In the case of an artificial eye, the mean refractive power of the eye A is set before the measurement. The artificial eye is located at the same distance from the position detector PSD 2 as the eye A. Moreover, as in the case of every normal measurement, the beam paths must be precompensated, and the diameter of the laser beam must be set. The light scattered by the diffuser plate SL is fed to the position detector PSD 2 at a small solid angle. The position detector PSD 3 downstream of the diffuser plate SL also monitors the measuring beam path so that an error in the optical beam path can easily be delimited. If the measurement result deviates from the expected value, this is an indication that the piezomotors PM 1, PM 2 and PM 3 are not functioning correctly and/or the liquid lenses FL 1 and FL 2 are not being correctly controlled.

During the normal measurement operation, the diffuser plate SL is removed from the beam path so that, in this case, the position detector PSD 3 monitors only the measuring beam in this case.

The position detectors PSD 1 to PSD 3 are limited in their bandwidth to values from 1.6 kHz to 16 kHz. Consequently, use is made of equalizers that compensate the linear distortions. The light energy, the light output and the position of the laser beam on the position detectors can be determined as quickly as possible with the aid of digital signal processors by means of fast sample and hold elements and fast analog-to-digital converters. The position detector PSD 1 calculates the position of the measuring beam on the front side of the measuring object (corresponding to the cornea in the case of the eye), whereas the position detector PSD 2 determines the position of the light scattered by the diffuser plate SL (corresponding to the retina in the case of the eye), and thus determines the local refractive power of the measurement object which is compared to the local desired refractive power by the position detector PSD 2. In the event of deviations from the local desired refractive power, the energy, the number of the laser pulses and the pulse duration of the laser pulses are calculated for the treatment laser LD 2 and transmitted to the latter such that it can carry out corrections at the eye.

The treatment beam of the treatment laser LD 2 is deflected in the X direction and/or Y direction with the aid of two scanners SC and coupled into the measuring and imaging beam paths with the aid of the beam splitter S 1. A further position detector PSD 4 monitors the energy, the pulse width and the output of the treatment laser LD 2, and simultaneously measures the current position of the laser beam of the treatment laser LD 2 and serves for adjusting the treatment, measuring and imaging beam paths.

The position detector PSD 4 can be used simultaneously to detect the position of the measuring beam on the measured object, such that the allocation of the measurement result to the treatment site is ensured. The position detector PSD 4 is at the same distance from the first beam splitter S 1 as the eye A.

The working distance of the treatment laser LD 2 is set via a lens L 4. In order to tune the working distance of the treatment laser LD 2 to the measuring distance of the measuring unit, further lenses L 5 and L 6 with imaging at a ratio 1:1 can be inserted into the measuring and/or imaging beam path between the beam splitters S 1 and S 3 in order to be able to set the measuring distance as desired.

The measuring device is simplified by mounting the aperture B, the second liquid lens FL 2 and the second position detector PSD 2 in common with the laser diode LD 1, the first liquid lens FL 1, the tilting mirror KS and the first piezomotor PM 1 on a positioning system in such a way that the optical axis of the imaging beam entering through the opening in the aperture B runs parallel to the optical axis of the measuring beam leaving the tilting mirror KS, it being possible to displace the positioning system in the direction of the optical axes by a further piezomotor.

A further simplification of the measuring device can be achieved by mounting the aperture B, the second liquid lens FL 2 and the second position detector PSD 2 in common with the tilting mirror KS on a positioning system in such a way that the axis of the imaging beam entering through the opening in the aperture B runs parallel to the optical axis of the measuring beam leaving the tilting mirror KS, the measuring beam coming from the laser diode LD 1 reaching the tilting mirror KS via the same optical axis as the deflected measuring beam that leaves the tilting mirror KS and it being possible to displace the positioning system by a piezomotor in the direction of the optical axes. Since only a few components are located on the positioning system, the piezomotor for driving the positioning system can be substantially smaller than in the example previously described.

The laying of the incoming measuring beam and the deflected beam into the same optical axis is possible by virtue of the fact that via the first liquid lens FL 1 the measuring beam coming from the laser diode LD 1 strikes a polarization cube, is reflected there and, passing via a λ/4 plate and the optical axis, reaches the tilting mirror KS, starting from where the deflected measuring beam, passing via the optical axis, the λ/4 plate, the polarization cube and a lens, strikes the eye A to be measured, starting from which the imaging beams dispersed at the retina pass via this lens and strike the polarization cube, are reflected there and, via a further lens and a reflecting beam splitter, reach the position detector PSD 2 through the aperture B and the liquid lens FL 2, while the beams reflected at the cornea of the eye A strike the beam splitter on the same path as the imaging beams and are let pass there so as to reach the observation camera BK 2 with telecentric lens via a further lens.

The last example differs from the penultimate one in that the linearly polarized laser beam is coupled in via the polarization cube. This has the advantage that the positioning system with the tilting mirror KS, the aperture B, the position detector PSD 2 and the liquid lens FL 2 is smaller and can thus be positioned in a faster fashion and more accurately. The laser diode and the liquid lens FL 1 are not movable.

The linearly polarized laser diode beam is reflected by the polarization cube toward the tilting mirror KS. The polarization direction is not changed by the polarization cube. It remains parallel to the mapping plane. The λ/4 plate produces circularly polarized light. Circularly polarized light that has merely changed the direction of rotation by 180° is reflected in the event of perpendicular incidence on the tilting mirror KS. The λ/4 plate converts the light into linearly polarized light. The direction of oscillation of the light is rotated by 90° relative to the linearly polarized laser diode light. The direction of oscillation is now perpendicular to the plane of the drawing. The polarization cube lets the light pass to the eye with this direction of oscillation without reflection.

Elliptically polarized light is produced if the circularly polarized light falls on to the tilting mirror at an angle, since both components (perpendicular and parallel) are reflected differently. Two components (perpendicular and parallel) of the elliptically polarized light coming from the tilting mirror KS are altered by the λ/4 plate. The light polarized perpendicularly to the mapping plane passes the beam splitter toward the eye without being reflected. The light polarized parallel to the mapping plane is reflected toward the laser diode by the beam splitter. The position and the light output of the laser beam can be detected with the aid of an additional mirror and a position detector.

Since the light that reaches the eye in the event of an oblique incidence of the light beam on the tilting mirror KS is modulated by the tilting mirror KS as a function of the incidence angle, the light output of the laser beam must be modulated in advance by control as a function of the tilting angle. The result of this is a measuring beam whose light output is independent of the tilting angle.

LIST OF REFERENCE SYMBOLS

A Eye
B Aperture
BK 1, BK 2 Observation camera
E Viewing opening
FL 1, FL 2 Liquid lens
KS Tilting mirror
L 1 to L 6 Lens
LD 1 Laser diode
LD 2 Treatment laser
PM 1 to PM 4 Piezomotor
PSD 1 to PSD 4 Position detector or camera
SC Scanner
S 1 to S 5 Beam splitter
SL Diffuser plate
V 1, V 2 Shutter

The invention claimed is:

1. A device for measuring imaging errors in a human eye, comprising:
    a laser diode emitting a scanning beam to the eye in an area-wide fashion, and reflecting beams reflected from the eye being measured and evaluated; and
    a treatment laser emitting a treatment laser for treating a surgical correction of a cornea and/or lens and/or a retina of the eye
    wherein positioned in a scanning and/or reflecting beam path, and a treating beam path is a first beam splitter,
    wherein inserted as a tilting mirror into the scanning beam path, between the laser diode and the first beam splitter, a 2D microscanner mirror, with aid of which the scanning beam is deflected in two dimensions for area-wide scanning of the optical system of the eye with frequencies from 150 Hz to 32 kHz, and
    wherein inserted into the scanning beam path, between the laser diode and the tilting mirror, is a first electrically controllable liquid lens with the aid of which a divergence and a diameter of the scanning beam is set.

2. The device as claimed in claim 1, wherein, inserted into the scanning beam path, between the tilting mirror and the first beam splitter, is a first lens whose distance from the tilting mirror is varied for precompensation of the scanning beam by a first piezomotor.

3. The device as claimed in claim 2, wherein, inserted into the scanning and/or reflecting beam path, between the first lens and the first beam splitter, is a second beam splitter, which decouples a portion of the measuring beam and feeds it to a first position detector or to a fast, sensitive first camera with or without an image intensifier, the detector or the camera is at a same distance from the second beam splitter as the optical system of the eye and detects a position of the scanning beam striking the cornea of the eye.

4. The device as claimed in claim 3, wherein, inserted into the scanning and/or reflecting beam path, between the second beam splitter and the first beam splitter, is a third beam splitter, which splits a beam path of the reflecting beams dispersed, by the retina of the eye, a first portion of the reflecting beams passing for a purpose of measuring refractive power of the optical system of the eye to a second position detector or to a fast, sensitive second camera with or without the image intensifier via a second lens and an aperture that delimit a solid angle of the reflecting beams path, and via a second electrically controllable liquid lens, adapting the reflecting beams with the second liquid lens to the second position detector and/or to the second camera, while a second portion of the reflecting beams passes to an observation camera equipped with a unit for recording eye movements and/or viewing movements of a test subject.

5. The device as claimed in claim 4, wherein, inserted into the scanning beam path, between the first lens and the second beam splitter, is a fourth beam splitter, which deflects the second portion of the reflecting beams reflected by the third and the second beam splitters to a second observation camera with telecentric lens for measuring the distance between a viewer of a measuring unit and the eye, and of checking a radius of curvature of the cornea of the eye.

6. The device as claimed in claim 4, wherein the eye is fixed with the aid of a optotype inserted in the form of a ring or a flashing point via the tilting mirror, setting the diameter of the ring or the flashing point with the aid of a first liquid lens and the tilting mirror.

7. The device as claimed in claim 4, wherein the second position detector or the second camera is axially displaced for adaptation of the reflecting beam by a second piezomotor.

8. The device as claimed in claim 4, wherein, inserted into the scanning and/or reflecting beam path, between the second beam splitter and the first position detector or the first camera, is a fifth beam splitter, which couples out a portion of the scanning beam and feeds it via a first shutter for self calibration to an artificial eye that is at the same distance from the second beam splitter as the optical system of the eye and consists of a third lens, a diffuser plate that is axially displaced by a third piezomotor, and a third position detector that is axially displaced by a fourth piezomotor, or a fast, sensitive third camera with or without image intensifier.

9. The device as claimed in claim 8, wherein distortions of electrical signals of the first, the second and the third position detector are compensated and amplified via electronic equalizing circuits or by means of software, local refractive force of the optical system of the eye being determined by calculating a difference between a measured value of the second position detector and a stored desired value.

10. The device as claimed in claim 8, wherein local refractive power of the optical system of the eye is determined by calculating a difference between a measured values of the second and the third position detector or the second and third camera.

11. The device as claimed in claim 1, wherein, inserted into the scanning beam path, between the tilting mirror and the first beam splitter, is a second beam splitter, which decouples a portion of the scanning beam and feeds it to a first position detector or to a fast, sensitive first camera with or without an image intensifier, the detector or camera being at a same distance from the second beam splitter as the optical system of the eve and detects a position of the scanning beam striking the cornea of the eye, wherein inserted into scanning and/or reflecting beam path, between the second beam splitter and the first beam splitter, is a third beam splitter, which splits a beam path of the reflecting beams dispersed by the retina of the eye, a first portion of the reflecting beams passing for measuring refractive power of the optical system of the eye to a second position detector or to a fast, sensitive second camera with or without the image intensifier via an aperture that delimit a solid angle of the reflecting beam path, and via a second electrically controllable liquid lens, adapting the reflecting beam with a second liquid lens to the second position detector and/or to the second camera, while a second portion of the reflecting beams passes to an observation camera that is equipped with a unit for recording eye movement and/or viewing movements of a test subject, and wherein a single lens is inserted into the scanning and/or reflecting beam path between the second beam splitter and the third beam splitter, whose distance from the tilting mirror is varied for precompensation of the scanning beam by a first piezometer.

12. The device as claimed in claim 2, wherein position of the tilting mirror is determined by sensors mounted on the tilting mirror.

13. The device as claimed in claim 4, wherein two scanners for deflecting the treatment beam in two directions running perpendicular to one another, and a fourth lens for setting a working distance between the treatment laser and the eye are inserted into a beam path of the treatment beam between the treatment laser and the first beam splitter.

14. The device as claimed in claim 4, wherein the first beam splitter couples out a portion of the treatment beam and feeds it to a fourth position detector or a fast, sensitive fourth camera with or without an image intensifier, the detector or camera is at a same distance from the first beam splitter as the optical system of the eye and measures energy, pulse width and output of the treatment laser and, moreover, simultaneously measures a current position of the treatment beam and adjusts the treatment, scanning and reflecting beam paths.

15. The device as claimed in claim 4, wherein, inserted into the scanning and or reflecting beam path, between the first and the third beam splitters for adaptation of a measuring distance to a treatment distance, are a fifth and a sixth lens whose scale ratio is set to 1:1.

16. The device as claimed in claim 4, wherein the device is integrated into a grinder and/or a polishing machine for optical lenses.

17. The device as claimed in claim 4, wherein the diameter of the first lens is adapted to the diameter of the of the eye being measured to measure local refractive power of any desired lenses.

18. The device as claimed in claim 4, wherein, in common with a laser diode, the first liquid lens, the tilting mirror and the first piezomotor, the aperture, the second liquid lens and the second position detector are mounted on a positioning system in such a way that an optical axis of the reflecting beam entering through an opening in an aperture runs parallel to the optical axis of the scanning beam leaving the tilting mirror, displacing the positioning system in a direction of the optical axes by a further piezomotor.

19. The device as claimed in claim 4, wherein, in common with the tilting mirror, the aperture, the second liquid lens and the second position detector are mounted on a positioning system in such a way that an optical axis of the imaging beam entering through an opening in an aperture runs parallel to the optical axis of the scanning beam leaving the tilting mirror, the scanning beam coming from a laser diode reaching the tilting mirror via a same optical axis as a deflected scanning beam that leaves the tilting mirror, and displacing the positioning system in a direction of the optical axes by a further piezomotor.

20. The device as claimed in claim 19, wherein, via the first liquid lens, the scanning beam coming from the laser diode strikes a polarization cube, is reflected there and, passing via a $\lambda/4$ plate, via the optical axis, reaches the tilting mirror, starting from which the scanning beam, which is deflected, passing via the optical axis, the $\lambda/4$ plate, a beam splitter cube and a lens, strikes the eye to be scanned, starting from which the reflecting beams dispersed at the retina pass via this lens and strikes the polarization cube, are reflected there and, via a further lens and a reflecting beam splitter, reach the position detector through the aperture and the liquid lens, while beams reflected at the cornea of the eye strike the beam splitter on a same path as the reflecting beams and are let pass there so as to reach the observation camera with telecentric lens via a further lens.

* * * * *